US010436862B2

United States Patent
Taniguchi et al.

(10) Patent No.: US 10,436,862 B2
(45) Date of Patent: Oct. 8, 2019

(54) MAGNETIC RESONANCE IMAGING APPARATUS

(71) Applicant: Hitachi, Ltd., Tokyo (JP)

(72) Inventors: Yo Taniguchi, Tokyo (JP); Hiroyuki Takeuchi, Tokyo (JP); Toru Shirai, Tokyo (JP); Suguru Yokosawa, Tokyo (JP); Shinji Kurokawa, Tokyo (JP); Hisaaki Ochi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 93 days.

(21) Appl. No.: 15/558,263

(22) PCT Filed: Apr. 7, 2015

(86) PCT No.: PCT/JP2015/060867
§ 371 (c)(1),
(2) Date: Sep. 14, 2017

(87) PCT Pub. No.: WO2016/162957
PCT Pub. Date: Oct. 13, 2016

(65) Prior Publication Data
US 2018/0081013 A1    Mar. 22, 2018

(51) Int. Cl.
G01R 33/385    (2006.01)
A61B 5/055     (2006.01)
G01R 33/48     (2006.01)

(52) U.S. Cl.
CPC .......... *G01R 33/3854* (2013.01); *A61B 5/055* (2013.01); *G01R 33/482* (2013.01)

(58) Field of Classification Search
CPC .... G01R 33/3854; G01R 33/482; A61B 5/055
See application file for complete search history.

(56) References Cited

U.S. PATENT DOCUMENTS

2013/0207653 A1    8/2013   Ito et al.
2015/0293197 A1*  10/2015   Taniguchi ............ G01R 33/543
                                                     324/309
2015/0309148 A1*  10/2015   Hardy ................ G01R 33/4826
                                                     324/309

FOREIGN PATENT DOCUMENTS

GB    2337125         11/1999
JP    01-249042 A     10/1989
(Continued)

OTHER PUBLICATIONS

F. Hennel, et al., "Silent" MRI With Soft Gradient Pulses, Magnetic Resonance in Medicine 42, 1999; pp. 6-10.
(Continued)

*Primary Examiner* — Rodney A Bonnette
(74) *Attorney, Agent, or Firm* — Mattingly & Malur, PC

(57) ABSTRACT

In an MRI apparatus, an imaging that produces almost no sound is implemented without extending an imaging time, not only for three-dimensional imaging, but also for two-dimensional imaging. A gradient pulse in a pulse sequence provided in the MRI apparatus is adjusted by using a basic waveform having a distribution of frequencies where strength dwindles substantially as the frequency increases from zero, and the waveform is convex upward or downward varying smoothly. An application time and strength are adjusted so that almost no sound is produced. Any imaging executable by a conventional pulse sequence can be implemented without producing almost any sound, using the conventional pulse sequence with little change.

13 Claims, 9 Drawing Sheets

(56) References Cited

FOREIGN PATENT DOCUMENTS

| JP | 07-227387 A | 8/1995 |
|----|-------------|--------|
| JP | 08-56918 A | 3/1996 |
| JP | 2008-302102 A | 12/2008 |
| WO | 2012/060192 A1 | 5/2012 |

OTHER PUBLICATIONS

Hennel, PhD, "Fast Gradient Echo MRI With Low Acoustic Noise", Journal of Magnetic Resonance Imaging 13, 2001, pp. 960-966.

Grodzki, et al., "Ultrashort Echo Time Imaging Using Pointwise Encoding Time Reduction With Radial Acquisition (PETRA)", Magnetic Resonance in Medicine 67, 2012, pp. 510-518.

International Search Report of PCT/JP2015/060867 dated Jul. 14, 2015.

International Preliminary Report on Patentability received in corresponding International Application No. PCT/JP2015/060867 dated Oct. 19, 2017.

* cited by examiner

MAGNETIC RESONANCE IMAGING APPARATUS

TECHNICAL FIELD

The present invention relates to a magnetic resonance imaging technique. More particularly, it relates to a technique for reducing sound that is produced by gradient magnetic fields.

BACKGROUND ART

A magnetic resonance imaging (MRI) apparatus is a medical-use diagnostic imaging system that generates nuclear magnetic resonance in hydrogen nuclei within any plane traversing a test subject and that performs tomographic imaging within the plane, based on nuclear magnetic resonance signals being generated. In general, a slice gradient magnetic field is applied for identifying an imaging plane, simultaneously with providing exciting pluses that excite magnetization within the plane. Accordingly, nuclear magnetic resonance signals (echoes) are obtained, which are generated at a stage of convergence of magnetization that has been excited. In addition, a phase encoding gradient magnetic field and a readout gradient magnetic field, being orthogonal to each other within the tomographic plane, are applied for providing the magnetization with positional information, during a period from the excitation until obtaining the echoes.

The pulses for generating echoes and each of the gradient magnetic fields are applied according to a predetermined pulse sequence. Various pulse sequences are known depending on purposes.

In those kinds of pulse sequences, in general, the gradient magnetic field in the trapezoidal waveform is turned on and off at high speed, and therefore, extremely loud sound, from 80 dB to 100 dB or larger, is produced within a bore. This sound has loudness considerably jarring the test subject placed in the bore, even though the test subject wears headphones or earplugs. Since this type of sound becomes louder as a magnetization level becomes higher, countermeasures are needed against a high magnetic-field machine of 3 T (tesla) or higher.

As one of sound reduction techniques, there is suggested a technique for varying the shape of gradient magnetic fields (see Non Patent Document 1, Non Patent Document 2, and the like). In general, sound produced by the gradient magnetic field is expressed by a product of a frequency response function (FRF) inherent to the device and a distribution of frequencies of the gradient magnetic field waveform. It is known that sound becomes smaller at a frequency having a small FRF value (Non Patent Document 1). Since the sound becomes extremely small, when the FRF value is 200 Hz or lower, there is disclosed a technique using a low-pass filter to suppress a frequency component of the gradient magnetic field waveform, in a range where the FRF exceeds that level, thereby reducing the sound. Specifically, for the sound reduction, it is suggested to allow the gradient magnetic field having a trapezoidal waveform, to pass through the low-pass filter, so as to smoothen the variation of strength at a rise time and a fall time of the wave.

It is further suggested in the Non Patent Document 2 that a readout gradient pulse and a phase encoding gradient pulse have sine waveforms.

The Non Patent Document 3 discloses an ultrashort echo time imaging technique aiming at producing almost no sound. This technique employs a radial type three-dimensional imaging method, using neither a slice selective gradient magnetic field nor a phase encoding gradient magnetic field, and varies strength of the remaining readout gradient magnetic field step-by-step, thereby eliminating on and off of the gradient magnetic field and suppressing sound production.

PRIOR ART DOCUMENT

Non Patent Document

Non Patent Document 1
Hennel F, Girard F, Loenneker T. "Silent" MRI With Soft Gradient Pulses. Magn Reson Med 1999; 42: 6-10.
Non Patent Document 2
Hennel F. Fast Spin Echo and Fast Gradient Echo MRI With Low Acoustic Noise. Journal of Magnetic Resonance Imaging 2001; 13: 960-966.
Non Patent Document 3
Grodzki D. Ultrashort Echo Time Imaging Using Pointwise Encoding Time Reduction With Radial Acquisition (PETRA). Magn Reson Med 2012; 67: 510-518.

DISCLOSURE OF THE INVENTION

Problems to be Solved by the Invention

The methods as described in the Non Patent Document 1 and in the Non Patent Document 2 produce a certain effect of noise reduction, by smoothening the rise and fall of the gradient pulse, or by employing a sine wave as a part of the gradient pulse. However, since a trapezoidal pulse or a pulse being smoothened only at the rise and fall time is employed, as the slice selective gradient pulse which is applied with the RF pulse, the state of "producing almost no sound" has not been achieved. Furthermore, those methods extend the time for applying the gradient pulse, resulting in that time lengths such as imaging time, echo time, and echo interval, are extended.

In the method as described in the Non Patent Document 3, since the readout gradient magnetic field is also applied during irradiation of the RF magnetic field, it is not possible to measure data in proximity to an origin of measurement space. Therefore, there is a problem that data items in proximity to the origin have to be measured individually point by point, and this may extend imaging time approximately by ten percent. In addition, this technique is based on the precondition that the radial three-dimensional imaging method is employed without using the slice gradient magnetic field, and therefore, it is not applicable to a two-dimensional imaging. Furthermore, since it is necessary to start reading out immediately after irradiation of the RF magnetic field, echo time is nearly zero all the time, and it cannot be set optionally.

The present invention has been made in view of the aforementioned conventional problems, and an object of the present invention is to achieve imaging that generates almost no sound, without extending the application time. The present invention is also applicable not only to three-dimensional imaging but also to two-dimensional imaging, also aiming at achieving the imaging that produces almost no sound. Another object of the present invention is to implement imaging where the echo time can be set optionally.

Means for Solving the Problems

In order to achieve the objects above, an MRI apparatus of the present invention employs pulses that produce almost no sound, as to all gradient pulses to be applied for imaging. Specifically, a gradient pulse having as a basic waveform, a pulse waveform with a distribution of frequencies where strength dwindles substantially as the frequency increases from zero, is used for all kinds of gradient pulses.

The basic waveform has an application time and/or strength which are optimized considering a noise level and an echo time.

It is to be noted that in the present invention, "almost no sound is produced" indicates that a difference in a noise level is equal to or less than 6 dB, between ambient noise while imaging is not performed and noise while imaging is performed (imaging is performed with applying the gradient pulses).

Advantage of the Invention

According to the present invention, a pulse that produces almost no sound is used for all the gradient pulses. In addition, the readout gradient magnetic field is not applied during irradiation of the RF magnetic field pulse, and therefore, it is possible to suppress sound producing also in the two-dimensional imaging, in addition to achieving silence in the three-dimensional imaging.

BRIEF DESCRIPTION OF THE DRAWINGS

FIG. 2(a) illustrates a sine squared waveform, and FIG. 2(b) illustrates a waveform described by Gaussian function;

FIG. 3(a) illustrates the sine-squared wave and a trapezoidal wave, FIGS. 3(b), 3(c), and 3(d) illustrate the distribution of frequencies for each application time;

FIG. 6(a) illustrates the pulse sequence, and FIG. 6(b) illustrates k-spatial arrangement of echoes;

FIG. 7(a) illustrates the pulse sequence, and FIG. 7(b) illustrates gridding;

BEST MODE FOR CARRYING OUT THE INVENTION

Figure 1:
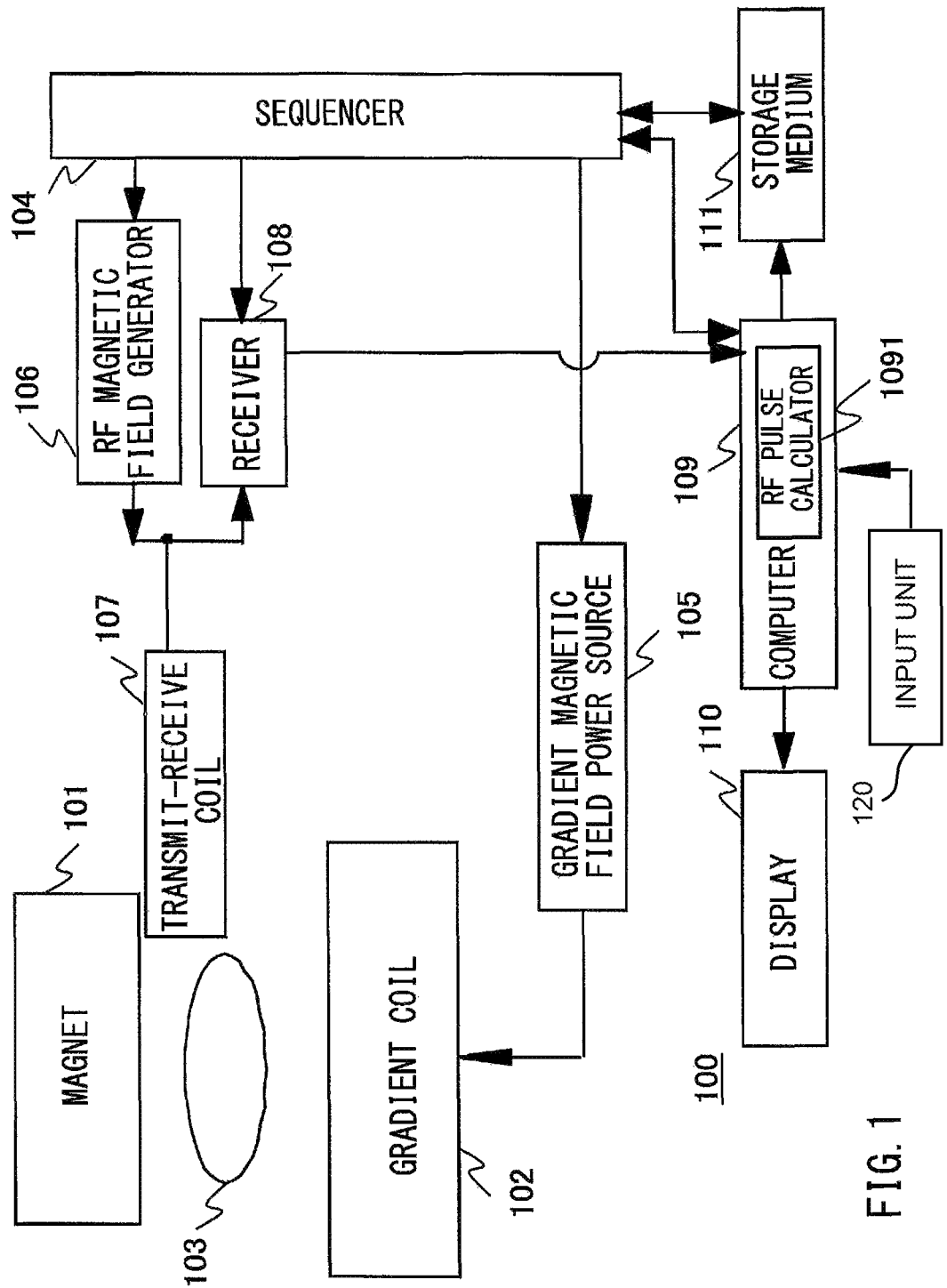
FIG. 1 is a block diagram showing a total overview of an MRI apparatus to which the present invention is applied.

An embodiment of an MRI apparatus and a method thereof according to the present invention will now be described. The MRI apparatus according to the present embodiment is provided with a magnetostatic magnet (101) configured to generate a static magnetic field, a gradient coil (102) configured to generate a gradient magnetic field within the static magnetic field generated by the magnetostatic magnet, an RF coil (107) configured to generate an RF magnetic field and to detect a nuclear magnetic resonance signal, a controller (104) configured to drive the gradient coil and the RF coil according to a predetermined pulse sequence, and a storage (111) configured to store the pulse sequence.

The pulse sequence stored in the storage (111) of this MRI apparatus, includes application of various gradient pulses, and every pulse included in all the various gradient pulses includes a pulse which is adjusted using a basic waveform having a distribution of frequencies where strength dwindles substantially as the frequency increases from zero.

The basic waveform may be used for all of the gradient pulses of respective types, or gradient pulses other than the aforementioned basic-waveform based gradient pulse may be included partially, as far as a condition of "almost no sound is produced" is satisfied. The basic waveform of the gradient pulse is a waveform convex upward or downward varying smoothly without any flat portion, and frequency strength at a frequency equal to or higher than 500 Hz, is zero, or substantially zero.

According to the present embodiment, the following magnetic resonance imaging method is provided. The magnetic resonance imaging method comprises irradiating an object placed in a static magnetic field with an RF magnetic field pulse and a gradient pulse, according to a predetermined pulse sequence, receiving a nuclear magnetic resonance signal generated from the object, and acquiring an image and/or a spectrum of the object by using the nuclear magnetic resonance signal, the method using as the gradient pulse included in the predetermined pulse sequence, a gradient pulse that is obtained by adjusting a basic waveform with a distribution of frequencies where strength dwindles substantially as the frequency increases from zero.

Since sounds perceived by humans depend on sensitivities, it is difficult to strictly define levels of sound. However, in general, when a sound pressure level increases by 10 dB (multiplied by 3.16), the sound level may be doubled approximately, even if it depends on frequencies, and when the sound pressure level increases by 6 dB (doubled), the sound level may become approximately one and half times higher. In the present embodiment, it is assumed that almost no sound is produced, when the sound pressure level increases by 6 dB or less (with respect to background noise).

With reference to FIG. 1, the MRI apparatus 100 of the present embodiment will now be described in detail. Hereinafter, in all the figures illustrating the embodiment of the present invention, elements with an identical function are labeled with the same reference numeral, and they will not be redundantly explained.

The MRI apparatus 100 of the present embodiment is provided with a magnet (static magnetic field magnet) 101, a gradient coil 102 for generating a gradient magnetic field, a sequencer (controller) 104, a gradient magnetic field power source 105, an RF magnetic field generator 106, a transmit-receive coil (RF coil) 107 for applying an RF magnetic field and detecting a nuclear magnetic resonance signal, a receiver 108, a computer (also serving as a part of the controller) 109, a display 110, and a storage medium (storage unit) 111.

The magnet 101 may be any of the following types; a permanent magnet, an electromagnet, and a super-conducting magnet. In the figure, a single block is shown, but various structures may be employed depending on the direction of the static magnetic field, such as separated vertically or horizontally, or a cylindrical structure. The gradient coil 102 may also have various structures, depending on the structure of the magnet 101 and the direction of the static magnetic field. The transmit-receive coil 107 has a single configuration in the figure, but the transmission coil and the receiver coil may be provided individually.

In the space of the static magnetic field generated by the magnet 101, a bed (not illustrated) is provided for placing a test subject (e.g., a living body) 103 thereon. The sequencer 104 transmits commands to the gradient magnetic field power source 105 and to the RF magnetic field generator 106, thereby generating a gradient magnetic field and an RF magnetic field, respectively. The gradient magnetic field gives gradients of the magnetic field to the space of the static magnetic field, thereby giving positional information to the nuclear magnetic resonance signals, and the gradient magnetic field is applied usually in the form of pulse.

The RF magnetic field is applied to the test subject 104 via the transmit-receive coil 107, and excites nucleus of atoms (hydrogen nucleus, in general) constituting the test subject 103. The transmit-receive coil 107 receives nuclear magnetic resonance signals generated from the test subject 103, according to the application of the RE' magnetic field, and transfers the signals to a receiver 108. The receiver 108 detects nuclear magnetic resonance signals by using a detection reference frequency (nuclear magnetic resonance frequency). The sequencer 104 sets the detection reference frequency that is used as a reference for detection. Signals being detected are transferred to the computer 109, and they are subjected to signal processing such as image reconstruction. The display 110 displays the result. The storage medium 111 may be allowed to store thus detected signals and measuring conditions as required.

The sequencer 104 usually exerts control over each of the units described above, so that they operate in accordance with pre-programmed procedures. Among the programs, a program particularly describing timing and strength of the RF magnetic field, the gradient magnetic field, and signal reception are referred to as a pulse sequence (imaging sequence). Various pulse sequences are developed in response to imaging methods, and they are put to practical use.

In the MRI apparatus 100 of the present embodiment, any of various pulse sequences is available, featuring a pulse sequence that includes a gradient pulse having a specific basic waveform is stored in advance, and this specific pulse sequence is used. The storage medium 111 stores this specific pulse sequence, in the same manner as other pulse sequences. It is alternatively possible that the storage medium 111 stores the basic waveform of the gradient pulse, the sequencer 104 adjusts this basic waveform in accordance with the strength and timing being programmed, and this basic waveform is used to execute the pulse sequence. The basic waveform of the gradient pulse and the pulse sequence will be described later in detail.

The computer 109 instructs the sequencer 104 to measure nuclear magnetic resonance signals (echoes) according to the predetermined pulse sequence, arranges thus measured echoes in k-space, and reconstructs an image from the echoes arranged in the k-space. The computer 109 accepts instructions from an operator, such as setting or changing of parameters of the pulse sequence, for instance, via an input unit 120 comprising a mouse, a keyboard, a touch panel, and the like, and according to those instructions, the computer is also capable of recalculating the pulse sequence, in particular, calculating the gradient pulse. FIG. 1 illustrates an RF pulse calculator 1091, as a function for performing RF pulse recalculation, which is a part of recalculation in the pulse sequence.

Next, there will be described a method for designing the pulse sequence that is stored in the storage medium 111 of the MRI apparatus according to the present embodiment.

Figure 2:
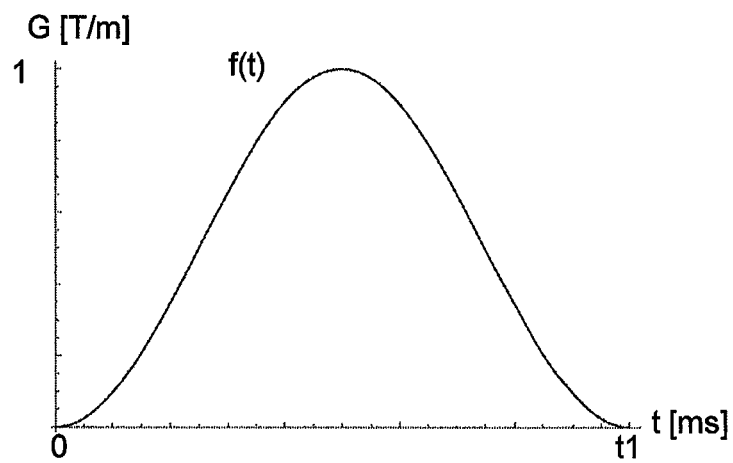
FIG. 2 illustrates a basic waveform of a gradient pulse.
Figure 2:
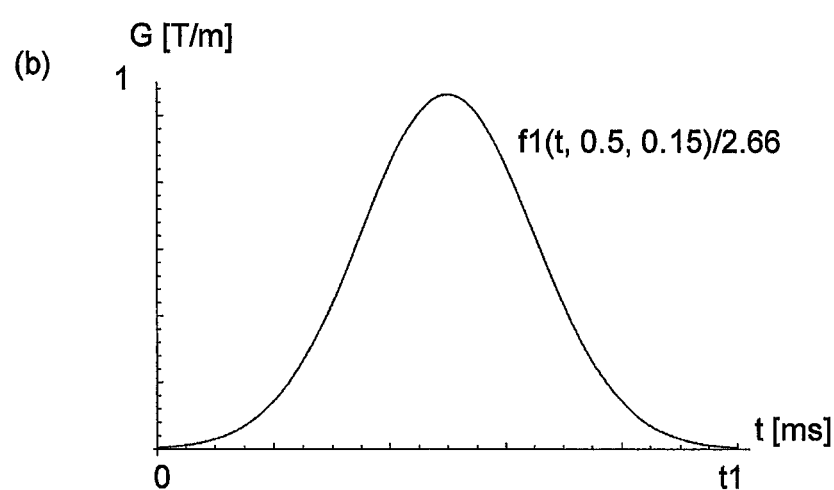

Firstly, the basic waveform of the gradient pulse included in the pulse sequence will be described. In the case of two-dimensional imaging, for example, the gradient pulse in the pulse sequence includes a slice selective gradient magnetic field, a phase encoding gradient magnetic field, a readout gradient magnetic field, and a crusher pulse. In the present embodiment, a gradient pulse used for all the various gradient magnetic fields has a waveform with a distribution of frequencies where strength dwindles substantially as the frequency increases from zero. The waveform with this kind of distribution of frequencies is only required to keep the frequencies to a low level, such as equal to a lower than several hundred Hz, and thus any waveform is applicable as far as the waveform is convex upward or downward varying smoothly, without any flat portion. Specifically, waveforms such as a half-cycle sine waveform or a sine squared waveform, and a Gaussian waveform, may be taken as example. Among those waveforms, the half-cycle sine squared waveform and the Gaussian waveform as shown in FIGS. 2(a) and 2(b) are suitable. In the graphs as shown in FIG. 2, the horizontal axis represents the application time, and the vertical axis represents the gradient magnetic field strength, and a maximum value of the gradient magnetic field strength indicates "1".

The sine squared waveform is expressed by the following formula 1:

[Formula 1]

$$f(t) = \begin{cases} a \cdot \sin^2(\pi t / t_1) & 0 \leq t \leq t_1 \\ 0 & \text{else} \end{cases} \quad (1)$$

where "a" is a height of the waveform, i.e., maximum strength of the gradient pulse, and "t1" is the application time of the gradient pulse. Considering parameters of the pulse sequence and a sound pressure level (level of produced sound), values of "a" and "t1" are determined so that suitable gradient pulse strength and application time are attained.

A waveform of the Gaussian function (normal distribution function) is expressed by the following formula 2:

[Formula 2]

$$f_1(t, m, s) = \frac{e^{-\frac{-m+t/t_1}{2s^2}}}{\sqrt{2\pi} \, s} \quad (2)$$

where "m" and "s" are an average and a standard deviation, respectively, and "$1/\sqrt{(2\pi)} \cdot s$" determines the height of the waveform, i.e., a maximum value of the gradient pulse. The value "m" is a half of the application time "t1". FIG. 2(b) shows a waveform when t1=1.0, and m=0.5, s=0.15 in the formula 2. Also in this case, considering parameters of the pulse sequence and the sound pressure level (level of produced sound), values are determined so that suitable gradient pulse strength and application time are attained.

There will now be described in detail, adjustment of the basic waveform, that is, a method for determining the gradient magnetic field strength and application time, considering the sound pressure level or the sound being produced.

Firstly, the application time can be determined, on the basis of a relationship between the application time and a distribution of frequencies of the basic waveform. The aforementioned distribution of frequencies of the basic waveform that is convex upward or downward varying smoothly, is a distribution where the strength becomes smaller (dwindles) as the frequency increases from zero. This distribution of frequencies varies depending on the application time of the gradient pulse, and as the application time becomes longer, the strength is reduced steeper, and the strength approaches zero over a wide range.

Figure 3:
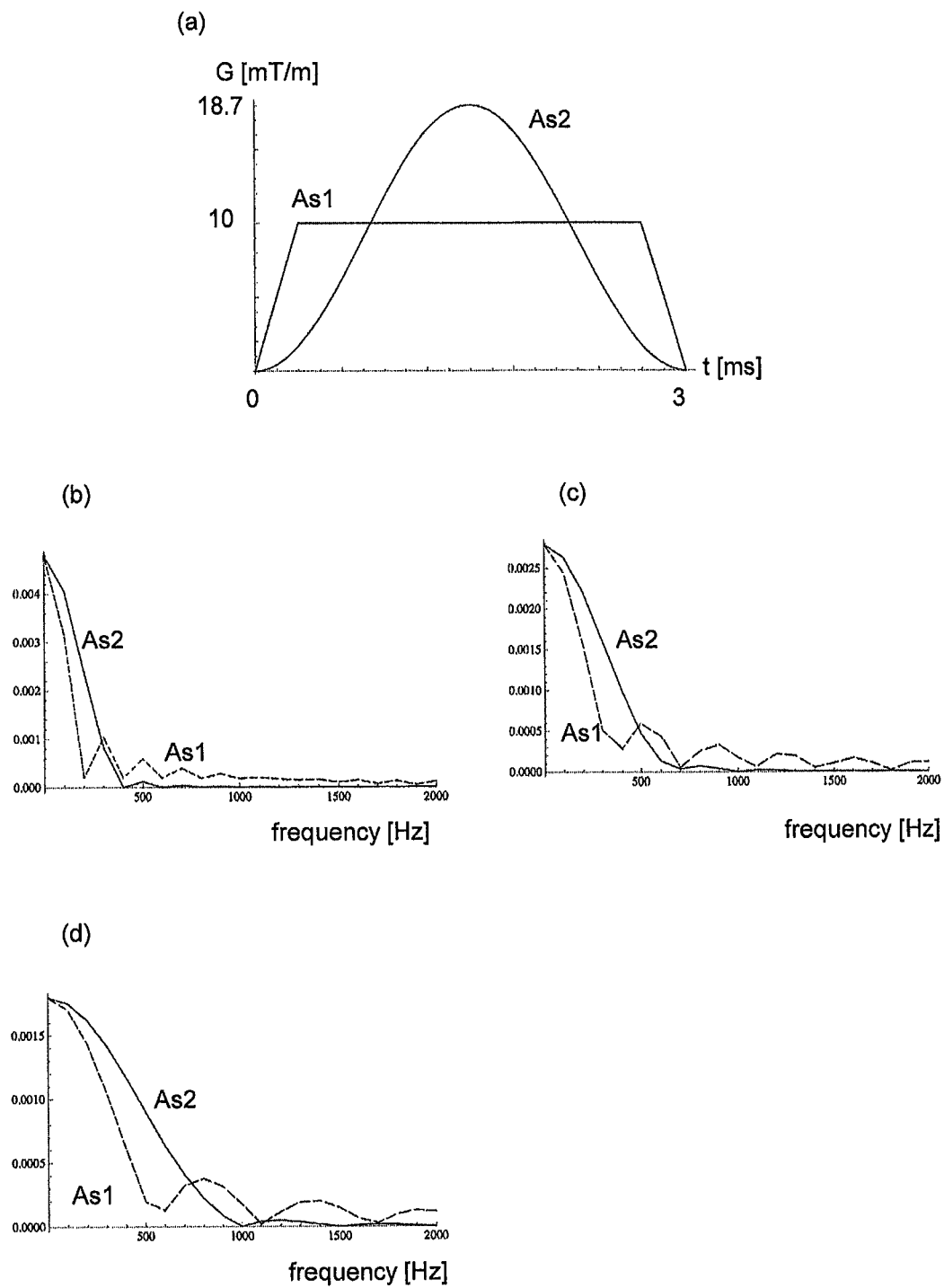
FIG. 3 illustrates a distribution of frequencies of a sine-squared wave.

FIG. 3 shows differences in the distribution of frequencies, when the application time varies as to the sine squared waveform. FIG. 3(a) shows a gradient pulse As1 of a conventional trapezoidal waveform, and a sine squared waveform As2 having the same area (the maximum strength is approximately 1.9 times higher than the trapezoidal wave) when the application time is 3 ms, and FIGS. 3(b) to 3(d) illustrate the distributions of frequencies of those waveforms, respectively, when the application time is 5 ms, 3 ms, and 2 ms. In the graphs as shown in FIGS. 3(b) to 3(d), the horizontal axis represents the frequencies, and the vertical axis represents the gradient magnetic field strength (in units of mT/m).

As shown in FIG. 3(b), when the application time is 5 ms, the waveform As2 shows that frequency components equal to or higher than 400 Hz indicates almost zero. A sound produced by the gradient magnetic field is determined by a product of a device-specific FRF and the distribution of frequencies of the gradient magnetic field waveform. In general, the FRF (frequency response function) of an MRI apparatus is extremely small, when the frequencies are equal to or lower than several hundreds of Hz, though there are differences depending on devices. Therefore, almost no sound is produced in the case where the application time is 5 ms, since the frequency components 400 Hz or higher become almost zero.

On the other hand, as shown in FIG. 3(c) and FIG. 3(d), if the application time is shortened such as 3 ms and 2 ms, higher frequency components become larger. When the application time is 3 ms, the frequency components around 500 Hz are kept to be almost zero. However, when the application time becomes 2 ms, the frequency components 500 Hz or higher become larger. Therefore, by setting the application time to 3 ms or longer, it is possible to perform imaging with almost no sound (with a difference of 6 dB or less, between background noise and noise when imaging is performed).

Figure 4:
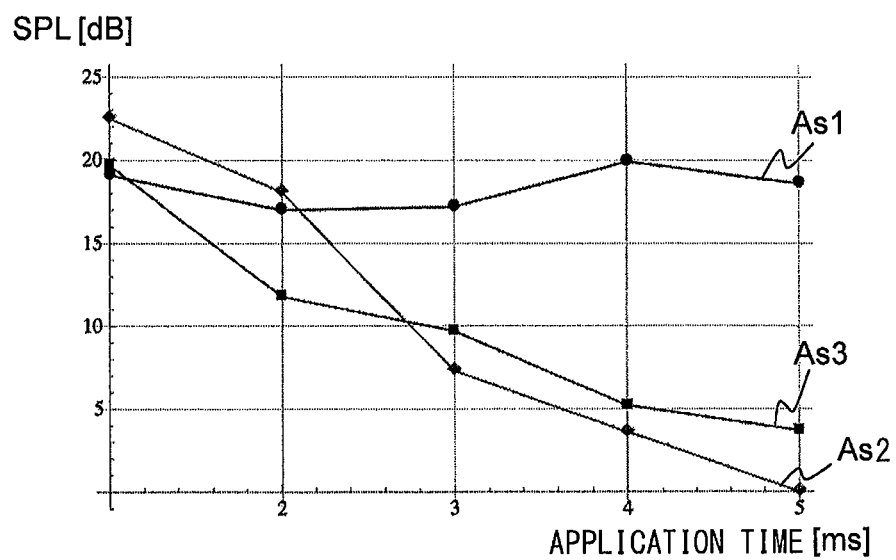
FIG. 4 illustrates a relationship between the application time and a sound pressure level of the gradient pulse.

FIG. 4 is a graph showing a relationship between the application time of the gradient magnetic field and a sound pressure level (values obtained by simulation). As described above, the sound pressure level depends on the frequency response function (FRF) of the device, and there is no large difference in this tendency device by device. In the simulation as shown in FIG. 4, FRF measured by 1.5 T device is employed by way of example. The horizontal axis of the graph in FIG. 4 represents the application time, and the vertical axis represents the sound pressure level calculated by the FRF of the device. Each waveform indicates values when the application time is changed from 1 ms to 5 ms incremented by 1 ms, being difference values relative to the sound pressure level of the sine-squared wave As2 when the application time is 5 ms. In the figure, As1 represents a trapezoidal wave, As3 represents a half-cycle sine wave having the same area as the trapezoidal wave (maximum strength is approximately 1.5 times higher than the trapezoidal wave), and As2 represents the sine-squared wave having the same area (maximum strength is approximately 1.9 times higher than the trapezoidal wave).

As seen from FIG. 4, the trapezoidal wave indicates a sound pressure level substantially constant, irrespective of the application time. On the other hand, as for the sine wave and the sine-squared wave, as the application time becomes shorter from 5 ms, the sound pressure level tends to rise. As for the sine-squared wave, when the application time is shorter than 3 ms, the sound pressure level becomes higher, relative to the trapezoidal wave and the sine wave. However, when the application time becomes 3 ms or longer, as for the sine-squared wave, the sound pressure level is lowered, relative to the trapezoidal wave and the sine wave, though the maximum strength of the sine-squared wave is larger than the other two waves. The largest reduction of the sound pressure occurs when the application time is 5 ms.

Accordingly, the sine-squared wave is the most preferable as the basic waveform, and the application time of the gradient pulse considering the FRF is preferably 3 ms or longer, and more preferably, it is 5 ms or longer.

Next, a method for determining the gradient magnetic field strength will be described. In general, the sound pressure level is proportional to static magnetic field strength, and it is also proportional to gradient magnetic field strength (maximum strength). By way of example, when the gradient magnetic field strength is doubled, the sound pressure level is also doubled (increased by 6 dB), and if the gradient pulse that is the same as the pulse used in the 1.5 T MRI apparatus, is applied in the MRI apparatus where the static magnetic field strength is 3 T, the sound pressure level is doubled compared to that in the 1.5 T apparatus (+6 dB). Therefore, under a certain condition of the static magnetic field strength, the gradient magnetic field strength is adjusted so that a targeted sound pressure level is attained (so that a difference from non-imaging time becomes 6 dB, for instance).

Specifically, it is possible to determine the gradient magnetic field strength that enables a targeted pressure level to be attained, with reference to the sound pressure level attained when imaging is performed under a certain imaging conditions. The sound pressure level under the imaging conditions used as the reference can be obtained in advance by simulation, or may be actually measured.

When the maximum gradient magnetic field strength under a reference imaging condition is assumed as G0, and the sound pressure level in that case is assumed as P0, a value M is obtained by converting a difference P (dB) between the sound pressure level P0 and the targeted pressure level, into a scaling factor of the sound pressure. Then, the gradient magnetic field strength G0 under the reference imaging condition is divided by the scaling factor M, and a resulting value is configured as maximum gradient magnetic field strength being settable. By way of example, when the sound pressure level is 63 dB for the imaging that uses the gradient pulse with the gradient magnetic field strength 10 mT/m and this sound pressure level is larger than the target value (e.g., 60 dB) by 3 dB, the value of 3 dB corresponds to the scaling factor 1.41 of the sound pressure level. Therefore, the gradient magnetic field strength is set to approximately 7 mT/m (=10 mT/m/1.41). When the sound pressure level is 60 dB for the imaging that uses the gradient magnetic field pulse with the gradient magnetic field strength 8 mT/m and it is less than the target value (e.g., 62 dB) by 2 dB, the value of −2 dB corresponds to the scaling factor 0.79 of the sound pressure level. Therefore, the gradient magnetic field strength can be set up to a higher value, approximately 10 mT/m (=8 mT/m/0.79).

Figure 5:
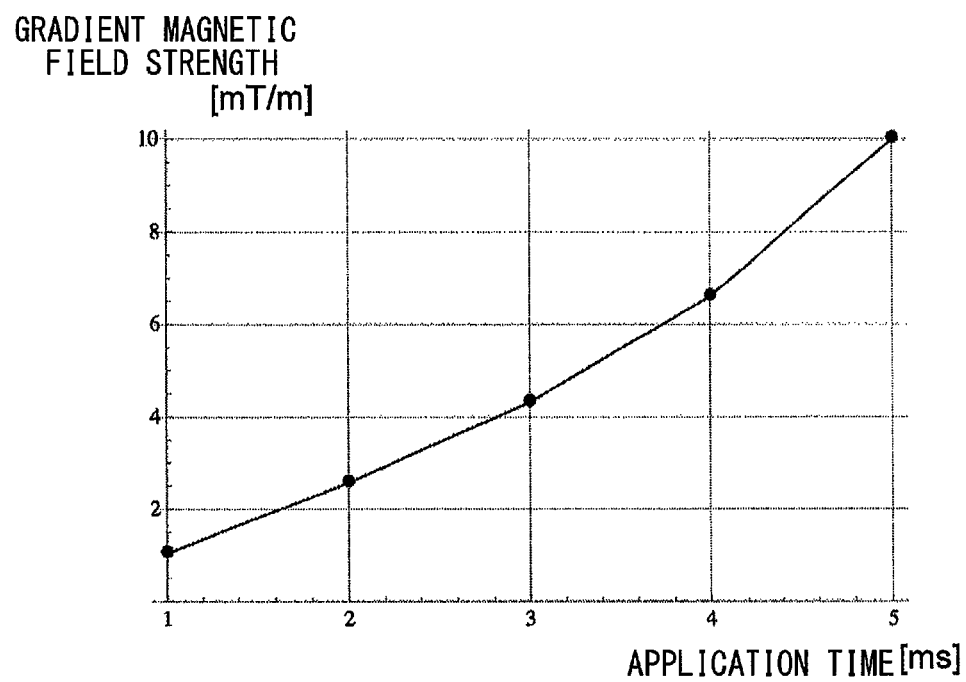
FIG. 5 illustrates a relationship between the application time of the gradient pulse and strength of the gradient magnetic field, at a predetermined sound pressure level.

As shown in FIG. 4, for the case of the sine wave and the sine-squared wave, the longer is the application time, the lower becomes the sound pressure level. On the other hand, the gradient magnetic field strength is proportional to the sound pressure level. Therefore, if both the application time and the gradient magnetic field strength are adjusted as variables, it is necessary to consider the relationship therebetween. FIG. 5 illustrates the relationship between the application time and the gradient magnetic field strength, when the sound pressure level is set to be constant (to a target value). The graph shown in FIG. 5 indicates maximum values of the gradient magnetic field strength, in the case where the sine wave is used when the application time is set to 1 ms and 2 ms, and the sine-squared wave is used when the application time set to other time. As seen from this graph, in order to keep the increase of sound pressure level to a certain value, it is necessary to reduce the maximum value of the gradient magnetic field strength, as the application time becomes shorter. For example, when the application time is 1 ms (it is equal to the case where a trapezoidal wave of any application time is used), it is necessary to set the gradient magnetic field strength to 1 mT/m or less, when the application time is 2 ms, the strength is to be 2.6 mT/m or less, when the application time is 3 ms, the strength is to be 4.3 mT/m or less, and when the application time is 4 ms, the strength is to be 6.6 mT/m or less.

In designing a pulse sequence, firstly gradient magnetic field strength is decided, for example, which makes the sound pressure to be a target level or less. Then, the pulse sequence can be designed by adjusting the application time, on the basis of an application amount of the gradient magnetic field that is determined by the pulse sequence and the gradient magnetic field strength decided above.

The computer 119 may perform calculation for this determination of the gradient pulse and designing of the pulse sequence, in accordance with the static magnetic field strength of the device, the pulse sequence to be executed, and parameters, and the like, set via the input unit 120, when the pulse sequence is executed. Alternatively, such information calculated in advance with respect to each pulse sequence, may be preprogrammed.

As for the gradient pulse, there are various gradient pulses, each having different application timing, application time, and strength, depending on a type of the pulse sequence. For example, if the pulse sequence is for two-dimensional imaging, basic gradient pulses may include a slice selective gradient magnetic field, a phase encoding gradient magnetic field, and a readout gradient magnetic field. In a non-Cartesian sequence, such as a radial sequence, biaxial or triaxial gradient magnetic field may be used, where the phase encoding gradient magnetic field is not distinguished from the readout gradient magnetic field. In the present embodiment, a gradient pulse that is determined on the basis of the aforementioned basic waveform is used for all those kinds of gradient pulses.

It should be noted that the present invention may not exclude a conventional trapezoidal gradient pulse, to be used as a part of the gradient pulses, instead of the gradient pulse of the aforementioned basic waveform, as far as it is low in strength and producing almost no sound. By way of example, trapezoid gradient pulses may be used as a part of the phase encoding gradient magnetic field or the slice encoding gradient magnetic field repeatedly applied with varying the gradient magnetic field strength every repetition time (TR).

There will now be described embodiments of the pulse sequence using the gradient pulse having this basic waveform.

<First Embodiment>

Figure 6:
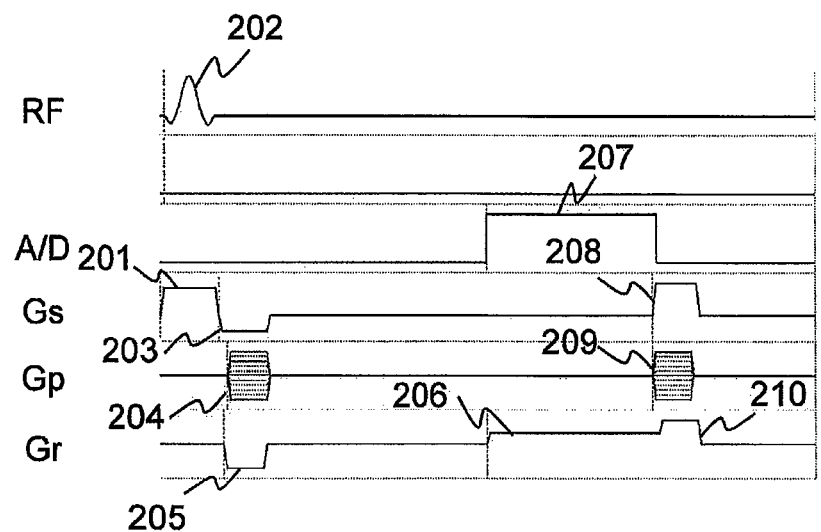
FIG. 6 illustrates an example of a pulse sequence of a general two-dimensional gradient echo type.
Figure 6:
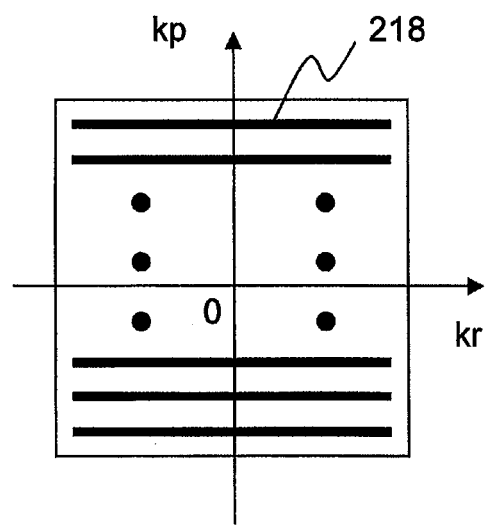
Figure 7:
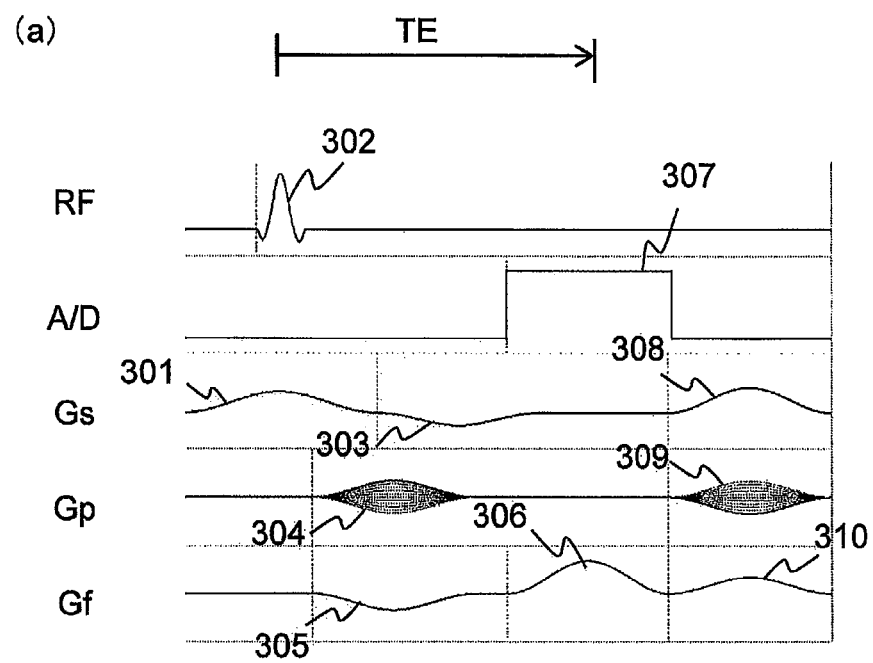
FIG. 7 illustrates one example of the pulse sequence according to the first embodiment.
Figure 7:
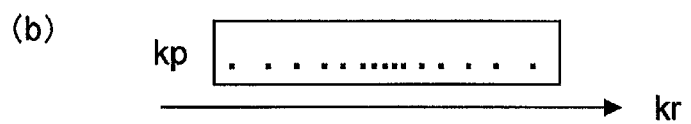
Figure 7:
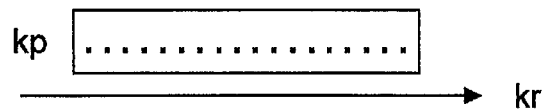

There will be described an embodiment where the present invention is applied to a pulse sequence according to the two-dimensional GrE (gradient echo) method. FIG. 6 shows a conventional two-dimensional GrE pulse sequence, and FIG. 7 shows a two-dimensional GrE pulse sequence according to the present embodiment. In those figures, RF, Gs, Gp, and Gr respectively represent an RF magnetic field, a slice gradient magnetic field, a phase encoding gradient magnetic field, and a readout gradient magnetic field. In the pulse sequence as shown in FIG. 6, each gradient pulse is a trapezoidal wave or a triangle wave.

The two-dimensional GrE pulse sequence of the present embodiment as shown in FIG. 7(a) is the same as the conventional two-dimensional GrE pulse sequence, except that the gradient magnetic field pulse having the aforementioned basic waveform being adjusted is used as the gradient pulse. Firstly, with reference to the two-dimensional GrE pulse sequence as shown in FIG. 6(a), an imaging method will be described.

Initially, irradiation of the RF magnetic field (RF) pulse 202 along with applying the slice selective gradient pulse 201 excites magnetization of a predetermined slice (cross-section) within a test subject 103. Next, there are applied the slice rephasing gradient pulse 203, the phase encoding gradient pulse 204 for adding positional information in the phase encoding direction to a magnetization phase, and the dephasing readout gradient magnetic field 205. Then, with applying the readout gradient pulse 206 for adding positional information in the readout direction, magnetic resonance signals (echoes) are measured within a sampling time (A/D) 207, and finally, crusher pulses 208, 209, and 210 are applied to three axes, Gs, Gp, and Gf. The time from irradiation of the RF magnetic field pulse 202 to an echo peak is referred to as an echo time TE. By varying the echo time, an image of desired contrast can be obtained. By way of example, by setting a short TE time (e.g., TE=10 ms), influence of T2 (transverse relaxation time) is reduced, thereby obtaining an image with the contrast emphasizing T1 (longitudinal relaxation time). On the contrary, when TE is made longer, an image of contrast emphasizing T2 can be obtained. The echo time can be set to any length, by changing the point of time (application starting time) of the readout gradient pulse 206.

The procedures above are repeated every repetition time TR, while varying the strength (phase encoding amount kp) of the phase encoding gradient pulse 204, and echoes are measured, the number of which is required for image reconstruction of a selected slice. The slice position can be changed by the frequency of the RF magnetic field pulse, and by repeating the measurement with varying the slice position, a set of echo signals corresponding to the number of slices can be obtained.

As shown in FIG. 6(b), the echoes 218 being measured are arranged in the k-space for each slice, and image is reconstructed by the inverse Fourier transform.

In the conventional pulse sequence as illustrated, the gradient pulse has a trapezoidal shape (As1 in FIG. 3), and therefore not a few components are included at the frequency of 500 Hz or higher as indicated by the dotted line in FIG. 3. In addition, though not illustrated, when using a pulse having a waveform including a flat portion even the rise and fall being smooth, as disclosed in the Non Patent Document 1 and the Non Patent Document 2, for example, there are some peaks in the components at a frequency less than 500 Hz, and those peaks may cause noise generation, even though components at the frequency of 500 Hz or higher can be decreased to almost zero. Furthermore, the application time of the gradient pulse is extended, resulting in that the imaging time, echo time, and echo intervals are also extended.

On the other hand, in the two-dimensional GrE pulse sequence according to the present embodiment, substantially all of the gradient pulses are replaced by the pulses having the waveforms as shown in FIGS. 2(a) and 2(b). That is, the slice selective gradient pulse 201 and the slice rephasing gradient pulse 203 are replaced by the slice selective gradient pulse 301 and the slice rephasing gradient pulse 303, the phase encoding gradient pulse 204 is replaced by the phase encoding gradient pulse 304, the dephasing readout gradient magnetic field 205 and the readout gradient pulse 206 are replaced by the dephasing readout gradient magnetic field 305 and the readout gradient pulse 306, and the crusher pulses 208, 209, and 210 are replaced by the crusher pulses 308, 309, and 310. FIG. 7 illustrates an example that the basic waveforms of those gradient pulses are sine-squared waves. As indicated by the solid line in FIG. 3, those pulses include almost no component at the frequency of 500 Hz or higher, and further, there are no protruding peaks in the components at the frequency less than 500 Hz. Therefore, those pulses generate almost no sound.

In the pulse sequence of the present embodiment, it is necessary to change the RF pulse 302 that is applied together with the slice selective gradient pulse 301, along with changing the form of the gradient pulses.

The RF pulse 302 is changed according to the formula (3-1).

[Formula 3]

$$b_{As2}(t) = b_{As1}(\tau(t)) f_{As2}(t)/f_{As1}(t) \quad (3\text{-}1)$$

$$\tau(t) = \int_0^t f_{As2}(t)/f_{As1}(t) dt \quad (3\text{-}2)$$

where "bAs2" is the RF pulse 302, "bAs1" is the original RF pulse 202, "fAs1" and "fAs2" are respectively strength of the gradient pulse 201 and strength of the gradient pulse 301, and "τ" is expressed by the formula (3-2) and referred to as a "time enhancement function".

Change of the RF pulse 302 is achieved according to the following procedures; when the pulse sequence according to the present embodiment is selected via the input unit 120, the computer 109 (RF pulse calculator 1091) recalculates the RF pulse 302 according to the formula (3-1) above, and when the pulse sequence is executed, the sequencer 104 controls the RF magnetic field generator 106, and thereby changing the RF pulse 302. Then, by using the pulse expressed by the formula (3-1) as the RF pulse 302, it is possible to selectively excite a slice plane in the same excited shape as obtained by a combination of the RF pulse 202 and the gradient magnetic field 201.

In addition, in the imaging using the pulse sequence of the present embodiment, when the image reconstruction is performed, it is necessary to perform gridding (rearrangement) of the echo signals that are acquired during application of the readout gradient magnetic field 306. In other words, strength of the readout gradient pulse 306 that is applied when echo signals are acquired is not constant. Therefore, echo sampling becomes non-uniform in the k-space, and they cannot be used as they are in the image reconstruction operation, such as commonly-used Fourier transform. Given this situation, at the time of image reconstruction, as shown in FIG. 7(b), non-uniformly sampled echo signals are converted into uniformly sampled signals according to gridding, and then a processing such as inverse Fourier transform is applied. This gridding method is well known in an imaging method that employs non-Cartesian sequence such as radial scanning, and thus description thereof will not be provided here.

The pulse sequence of the present embodiment is the same as the aforementioned two-dimensional GrE pulse sequence conventionally used, except that the gradient pulses are replaced and accordingly the RF pulse is changed and gridding is performed. Therefore, while varying the strength of the phase encoding gradient pulse 304 (and the pulse 309), the pulse sequence is repeated a predetermined number of times, every repetition time (TR), and a set of echoes are obtained for each slice.

In the present embodiment, substantially every gradient pulse is made to have a predetermined basic waveform that has been adjusted so as to produce almost no sound, thereby enabling noise-suppressed imaging.

The pulse sequence of the present embodiment includes two types of gradient magnetic fields, and they are different in starting and ending the pulse application, based on the relationship with the RF pulse. One type starts application before one RF pulse, and ends application after irradiation of the RF pulse, like the slice gradient pulse 301. The other types start and end application, without applying the RF pulse therebetween, like the pulses other than the slice gradient pulse 301. In any of the types, similar to the trapezoidal wave used in an ordinal sequence, two or more RF pulses are not applied between the application start and the application end, and the application time is set to be shorter than the repetition time (TR). With this configuration, imaging can be implemented under the conditions similar to those used in the conventional sequence, without producing almost any sound. Therefore, there is no extension of imaging time. In addition, since the time for starting the readout gradient pulse 306 can be set freely, the echo time TE is also settable to any length. In addition, since the pulse sequence of the present embodiment is different from the conventional pulse sequence, only in the point that the gradient pulses are replaced, there is no possibility that any gradient magnetic fields other than the slice selective gradient magnetic field will be applied, during the time when the RF pulse is applied. Therefore, it is not necessary to shorten the application time of the RF pulse, and the same application time as in the conventional sequence can be secured. If the application time of the RF pulse is reduced, a high-power amplifier is required to intensify the RF pulse, but such high-power amplifier is needless.

<Example of the First Embodiment>

A pulse sequence as shown in FIG. 7 was designed, using every gradient pulse having a sine-squared waveform as the basic form, with the application time of 5 ms, the gradient pulses respectively having the same area as the gradient pulses in the conventional two-dimensional GrE sequence (FIG. 6). The repetition time (TR) was 20 ms. The strength of the gradient pulses was from 2.5 mT/m to 8 mT/m.

This pulse sequence was executed in the MRI apparatus having the static magnetic field strength of 1.5 T (hereinafter, briefly referred to as 1.5 T apparatus), and when A-weighted sound pressure level was measured (average in 20 seconds), it was 63 dB. The sound pressure level (background noise) prior to executing the sequence was 59 dB. Increase of the sound pressure level caused by the imaging was 4 dB. Increase of the sound pressure level by 4 dB is equal to approximately 1.58 times increase, but since the sound increase perceivable by humans is lower than that level, it can be said that almost no sound was produced by the increase of 4 dB.

In this example, if a permissible value of increase of the sound pressure level is set to +6 dB with respect to the background noise, there is an allowance of 2 dB (1.26 times increase). Therefore, even though the maximum strength of the gradient pulse is raised from 8 mT/m to 10 mT/m, imaging with the allowance of +6 dB, that is, imaging that produces almost no sounds, is possible.

According to the relationship between the application time and the sound pressure level as shown in FIG. 4, when the application time of the pulse is reduced from 5 ms, to 4 ms, and to 3 ms, the sound pressure level is increased to 4 dB and to 7 dB, respectively. Therefore, when the application time of the pulse in this sequence is set to 4 ms and to 3 ms, the sound pressure level is increased to 10 dB and to 13 dB, respectively, and it is predictable that the sound pressure level exceeds the allowance.

It is assumed that the 1.5 T apparatus is used in the present example. If the sequence of this example is executed in a 3T apparatus, the sound pressure level is increased with respect to the background noise by 6 dB (doubled) relative to the 1.5 T apparatus, and it becomes approximately 10 dB. In order to perform silent imaging, it is only required to set the strength of each gradient pulse 0.63 times higher (−4 dB), for example, so as to suppress this increase of the sound pressure level to 6 dB or lower. In this case, it is necessary to set the gradient magnetic field strength to be approximately 5 mT/m or less.

Assuming from the relationship between the application time and the sound pressure level as to each waveform, as shown in FIG. 4, the sine wave and the trapezoidal wave when the application time is 5 ms, show the increase of sound pressure level, +4 dB and +19 dB, respectively with respect to the sine squared wave of the same application time. Therefore, when the sine-squared wave of this example is changed to the sine wave or to the trapezoidal wave, it is predictable that the sound pressure level increases from 63 dB, respectively to around 67 dB (+8 dB: 2.51 times higher with respect to the background noise) and to around 82 dB (+23 dB: at least 10 times higher with respect to the background noise).

<Second Embodiment>

Figure 8:
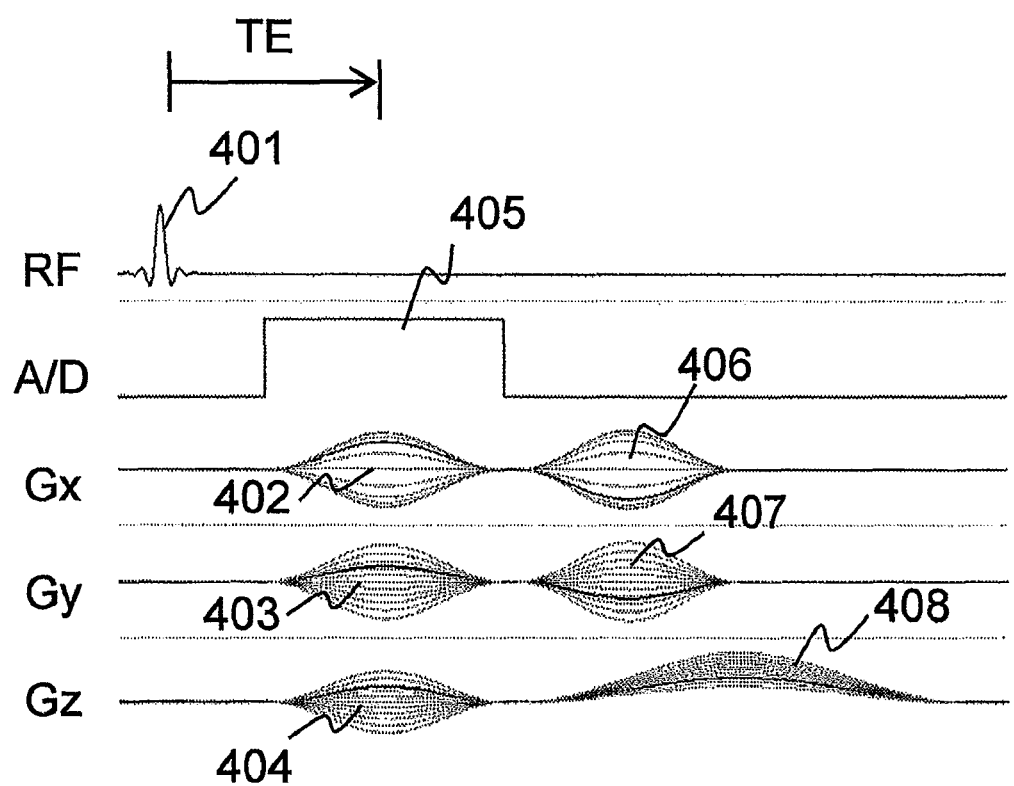
FIG. 8 illustrates one example of the pulse sequence according to a second embodiment.

There will be described a second embodiment where the present invention is applied to a three-dimensional imaging sequence. By way of example, FIG. 8 shows a radial-type GrE sequence.

In this pulse sequence, an object is irradiated with an RF magnetic field (RF) pulse 401, and magnetization within the object is excited. Subsequently, while readout gradient pulses 402, 403, and 404 are applied respectively to three axes Gx, Gy, and Gz, echoes are measured in the sampling period (A/D) 405. Finally, rephasing gradient pulses 406 and 407 are applied to the two axes Gx and Gy, and a composite pulse 408 of the rephasing pulse and a crusher pulse is applied to the axis Gz. The sequence above is repeated every repetition time (TR) (e.g., 20 ms), while varying strength of each of the gradient pulses. In this example, the crusher pulse is applied only to the Gz axis, but the crusher pulse may be applied to any axis other than the Gz axis, or it may be applied not only to one axis, but also to two or three axes.

Since this pulse sequence does not use a slice selective gradient pulse, a publicly known non-selective pulse can be used as the RF pulse 401. However, sampling is a radial type and non-uniform, and therefore three-dimensional gridding is used when image reconstruction is performed.

The pulse sequence of the present embodiment also uses the gradient pulse having the basic waveform as shown in FIG. 2, for every type of the gradient magnetic field. However, the present embodiment does not exclude using a trapezoidal gradient pulse for a part of various gradient magnetic fields, for example, as far as the gradient magnetic field strength is small and there is no sound produced or the sound is ignorable even if the gradient pulse has the trapezoidal shape.

Also in the pulse sequence of the present embodiment, every gradient pulse can be applied within the time shorter than the repetition time of the sequence, without applying two or more RF pulses between the application start and the application end. Accordingly, the pulse sequence can be executed under the same imaging conditions as in the conventional sequence, without producing almost any sound. In addition, similar to the first embodiment, the echo time TE is settable to any time.

<Example of the Second Embodiment>

The three-dimensional radial-type GrE sequence of as shown in FIG. 8 was designed, setting the application time of the gradient pulses 402, 403, 404, 406, and 407 to 5 ms, and setting the application time of the pulse 408 to 10 ms. The gradient magnetic field strength of the gradient pulses 402, 403, 404, 406, and 407 was from 3.8 mT/m to 4.3 mT/m, and the strength of the pulse 408 with the application time 10 ms was 6.0 mT/m.

This pulse sequence was executed in the 1.5 T apparatus, and the A-weighted sound pressure level being measured (average in 20 seconds) was 61 dB. Increase of the sound pressure level was 2 dB relative to the sound pressure level prior to executing the sequence 59 dB (background noise), and it can be said that almost no sound was produced.

When the application time of the pulse 408 was set to 5 ms and the strength was set to 12 mT/m, the sound pressure level was 69 dB, and sound was increased by 10 dB (3.16 times larger) relative to the background noise. In this case, it is hard to say that almost no sound was produced. In order to suppress the sound pressure level to an allowable increase amount of 6 dB (two times larger), it is sufficient to reduce the gradient magnetic field 12 mT/m to 7.6 mT/m, which is 0.63 times (−4 dB). As described in the aforementioned example, if it is reduced to 6.0 mT/m, the pulse sequence that produces almost no sound can be achieved.

In the example of the first embodiment, if the strength was made to 8 mT/m or lower, almost no sound was produced. If the two examples are considered together, in order to implement the pulse sequence that produces almost no sound, it is necessary to set the strength of the gradient pulse to approximately 10 mT/m or less.

In addition, in the embodiments as described so far, the repetition time (TR) of the pulse sequence has not been referred to, but the longer is the repetition time, the sound pressure level tends to be lowered. Therefore, if the repetition time is made longer, it is also possible to reduce the sound production. However, that effect seems to be relatively small, and in the example of the first embodiment, when the repetition time 20 ms was doubled to 40 ms, the sound pressure level was lowered approximately 1 dB only.

<Embodiment of User Interface>

The MRI apparatus of the present embodiment is further provided with an input unit configured to input pulse-sequence conditions by a user, featuring that a controller adjusts gradient pulses each using a basic waveform, under the conditions that are inputted via the input unit. In the aforementioned embodiments, the pulse sequences designed in advance are stored in the storage medium 111. The user is allowed to select a pulse sequence via the input unit 120, and to set its parameters (such as echo time, repetition time, and image field of view, for instance), thereby executing the pulse sequence. In this case, the user may be allowed to select the pulse sequence via the input unit 120, also considering higher priority among elements, such as imaging time, noise, and "dB/dT" (a rise of the gradient magnetic field).

Figure 9:
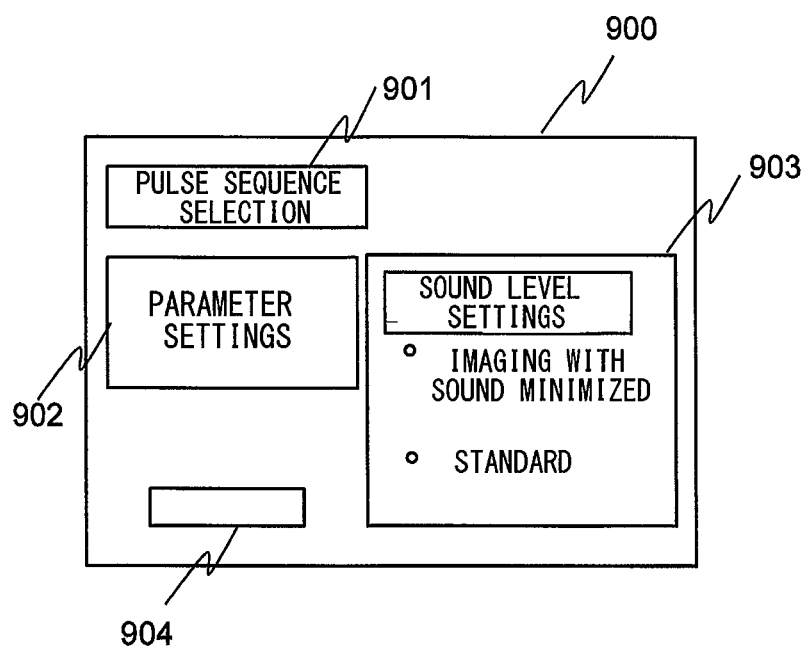
FIG. 9 illustrates a display example of a user interface.

FIG. 9 illustrates a user interface (UI) example of the input unit (the input unit including a display) that allows selection by the user. In this example, there is shown in a parameter setting screen 900, in addition to a pulse sequence selection block 901 and a parameter setting block 9 a UI in the form of sound level setting block 903 that allows the user to select a pulse sequence considering a level of produced sound. When the "Imaging with sound minimized" is selected, a pulse sequence that is designed to set the sound level increase, for instance, to "+4 dB" or "+6 dB" from background noise, is selected and executed. On the other hand, when "Standard (imaging with sound production permitted)" is selected, a basic pulse sequence using a trapezoidal waveform, for instance, is executed. In this example, selection from two levels is shown, but it is also possible to enable setting from three or more levels.

A storage medium may store the pulse sequences, the number of which corresponds to the number of sound levels selectable by the user, or a basic pulse sequence having the trapezoidal wave and a "no sound producing" pulse sequences using a particular basic waveform are stored, and as for the latter pulse sequences, the gradient magnetic field strength and the application time may be readjusted in accordance with the selected sound level. If there is an inconsistency between conditions of the gradient pulse of the selected level and parameters of the pulse sequence being provided, it is possible to display the notice in the block 904, for instance, and further to prompt the user to select a priority level.

So far, there have been described embodiments of the present invention, and the present invention features that a gradient pulse that produces substantially almost no sound is used for every type of gradient pulse included in the pulse sequence. Here, the pulse sequence is not limited to the GrE sequence or the radial GrE sequence described in the embodiments, but it is applicable to any publicly known pulse sequence. Furthermore, the pulse sequence is applicable not only to imaging for acquiring a morphological image, but also to any imaging using gradient magnetic field, including an imaging for obtaining a spectrum such as MRSI, and imaging for acquiring a phase image.

INDUSTRIAL APPLICABILITY

According to the present invention, it is possible to achieve imaging that produces almost no sound, without extending the application time, not only for three-dimensional imaging but also for two-dimensional imaging.

DESCRIPTION OF SYMBOLS

101 . . . magnet (magnetostatic magnet), 102 . . . gradient coil, 103 . . . test subject, 104 . . . sequencer (controller), 105 . . . magnetic field gradient power supply, 106 . . . RF magnetic field generator, 107 . . . RF coil, 108 . . . receiver, 109 . . . computer, 1091 . . . RF pulse calculator, 110 . . . display, 111 . . . storage medium, 120 . . . input unit

What is claimed is:

1. A magnetic resonance imaging apparatus, comprising:
a magnetostatic magnet configured to generate a static magnetic field;
a gradient coil configured to generate a gradient magnetic field within the static magnetic field generated by the magnetostatic magnet;
a radio frequency (RF) coil configured to generate a RF magnetic field and to detect a nuclear magnetic resonance signal;
a controller configured to drive the gradient coil and the RF coil according to a pulse sequence including a plurality of gradient magnetic field pulses, and
a storage medium configured to store the pulse sequence,
wherein each of the gradient pulses is a half-cycle sine waveform, a sine squared waveform, or a Gaussian waveform having a distribution of frequencies where strength dwindles above 500 Hz, and
wherein each of the gradient pulses has a pulse application time of 3 ms or more.

2. The magnetic resonance imaging apparatus according to claim 1, wherein,
each of the gradient pulses is convex upward or downward varying smoothly and without any flat portion.

3. The magnetic resonance imaging apparatus according to claim 1, wherein,
each of the gradient pulses has a gradient magnetic field strength of 10 mT/m or less.

4. The magnetic resonance imaging apparatus according to claim 1, wherein the controller is configured to determine a pulse of the RF magnetic field generated by the RF coil according to a slice selective gradient pulse of the gradient pulses.

5. The magnetic resonance imaging apparatus according to claim 4, wherein,
the controller applies the pulse of the RF magnetic field pulse between a start of application time and an end of application time of the slice selective gradient pulse.

6. The magnetic resonance imaging apparatus according to claim 1, wherein,
the pulse sequence is a two-dimensional imaging pulse sequence that uses a slice selective gradient magnetic field.

7. The magnetic resonance imaging apparatus according to claim 1, wherein,
the pulse sequence is a three-dimensional imaging pulse sequence.

8. The magnetic resonance imaging apparatus according to claim 7, wherein,
the three-dimensional pulse sequence is a three-dimensional radial sequence.

9. The magnetic resonance imaging apparatus according to claim 1, wherein,
the controller further comprises an input unit configured to input a condition of the pulse sequence, and adjusts the gradient pulses according to the condition thus inputted via the input unit.

10. The magnetic resonance imaging apparatus according to claim 1, wherein,
wherein a sound pressure level at the pulse application time of each of the gradient pulses is less than +6 dB with respect to a sound pressure level of a non-imaging time.

11. The magnetic resonance imaging apparatus according to claim 1, wherein, the sound pressure level at the pulse application time of each of the gradient pulses is less than +4 dB with respect to a sound pressure level of a non-imaging time.

12. The magnetic resonance imaging apparatus according to claim 1, wherein,
one or more of the gradient pulses has a pulse application time of 5 ms or more, and
one or more of the gradient pulses has the distribution of frequencies where strength is approximately zero above 400 Hz.

13. The magnetic resonance imaging apparatus according to claim 1, wherein,
each of the gradient pulses has a pulse application time of 5 ms or more, and
each of the gradient pulses has the distribution of frequencies where strength is approximately zero above 400 Hz.

* * * * *